United States Patent
Dony et al.

(10) Patent No.: US 6,890,897 B1
(45) Date of Patent: May 10, 2005

(54) USE OF A MELANOMA INHIBITING ACTIVITY FACTOR (MIA) FOR CARTILAGE AND BONE REPAIR

(75) Inventors: Carola Dony, München (DE); Gabriele Proetzel, Schwanfeld (DE); Ulrike Leser-Reiff, Penzberg (DE)

(73) Assignee: Scil Technology GmbH, Martinsried (DE)

( * ) Notice: Subject to any disclaimer, the term of this patent is extended or adjusted under 35 U.S.C. 154(b) by 0 days.

(21) Appl. No.: 09/806,635

(22) PCT Filed: Jan. 27, 2000

(86) PCT No.: PCT/EP00/00623

§ 371 (c)(1),
(2), (4) Date: Jun. 4, 2001

(87) PCT Pub. No.: WO00/44401

PCT Pub. Date: Aug. 3, 2000

(30) Foreign Application Priority Data

Jan. 28, 1999 (EP) .............................. 99101315

(51) Int. Cl.$^7$ ......................... A61K 38/00; A61K 39/00; A61K 9/14; C07K 14/00
(52) U.S. Cl. ........................ 514/2; 530/350; 424/198.1; 424/424
(58) Field of Search ............................. 514/2; 530/350; 424/198.1, 484

(56) References Cited

U.S. PATENT DOCUMENTS

| | | | | | |
|---|---|---|---|---|---|
| 4,919,929 A | * | 4/1990 | Beck | ........................ | 424/157.1 |
| 5,770,366 A | * | 6/1998 | Bogdahn et al. | ............... | 435/6 |
| 6,150,118 A | * | 11/2000 | Bosserhoff et al. | .......... | 435/7.1 |
| 6,331,312 B1 | * | 12/2001 | Lee et al. | ................... | 424/426 |

FOREIGN PATENT DOCUMENTS

| | | |
|---|---|---|
| WO | 92 09697 A | 6/1992 |
| WO | 95 03328 A | 2/1995 |
| WO | 98 30234 A | 7/1998 |

OTHER PUBLICATIONS

Zhou et al., Genes and Development, 1997, vol. 11, pp. 2191-2203.*
BioRad Catalogue, 1992.*
Bosserhoff, et al., "Structure and Promoter Analysis of the gene encoding . . . MIA", Journ. of Biological Chemistry, vol. 271, No. 1.
Bosserhoff, et al. "Melanoma–Inhibiting Activity, a Novel Serum . . . Melanoma", Cancer Research, vol. 57, No. 15.

* cited by examiner

Primary Examiner—Janet Andres
(74) Attorney, Agent, or Firm—Fulbright & Jaworski LLP

(57) ABSTRACT

A melanoma inhibiting activity factor (MIA), preferably in combination with an osteoinductive protein, is a useful pharmaceutical agent for promoting bone healing and/or cartilage repair.

13 Claims, No Drawings

USE OF A MELANOMA INHIBITING ACTIVITY FACTOR (MIA) FOR CARTILAGE AND BONE REPAIR

The present invention relates to a method and a composition for the induction of the chondro-/osteogenic lineage from mesenchymal stem cells and for promoting cartilage and bone formation using a melanoma inhibiting activity factor (MIA) preferably in combination with an osteoinductive protein.

MIA was initially described as a factor inhibiting the growth of malignant melanoma cell line HTZ-19 (Weilbach et al., Cancer Res. 50 (1990) 6981–6986). Cloning and purification of the factor resulted in a novel 11 kD protein with anti-tumor activity (WO 95/03328). The bovine homolog CD-RAP (cartilage derived-retinoic acid-sensitive protein) was detected in cartilage primordia and cartilage (Dietz, U., and Sandell, L., J. Biol. Chem. 271 (1996) 3311–3316). The mouse CD-RAP/MIA gene was localized in embryonic mouse cartilage and the transcripts were detected in chondrosarcomas (Bosserhoff et al., Developmental Dynamics 208 (1997) 516–525). These data point to a normal expression of MIA in cartilage. Further data are derived from transgenic mice where MIA promoter directs the cartilage specific expression of lacZ (Xie et al., 44$^{th}$ Annual Meeting, Orthopaedic Research Society, Mar. 16–19, 1998, New Orleans, La.). MIA could also be used as a progression marker for malignant melanoma (Bosserhoff et al., Cancer Research 57 (1977) 3149–3153; DE 196 53 358 A1).

Osteoinductive proteins are proteins which induce the full developmental cascade of endochondral bone formation towards chondrocytes and osteocytes and are, for example, hedgehog proteins (Sonic (Shh), Indian (Ihh), Desert (Dhh); Kinto et al., Kinto et al., FEBS Letters 404 (1997) 319–323), or members of the bone morphogenetic protein family (BMPs).

Hedgehog proteins, especially sonic hedgehog (Shh) are responsible for the development of multiple organ systems, including brain, spinal cord, craniofacial structures, limbs, the eye, left and right body symmetry, somite patterning (Hammerschmidt et al., Trends Genet. 13 (1997) 14–21). Indian hedgehog (Ihh) plays a role in cartilage development (Vortkamp et al., Science 273 (1996) 613–622; Lanske et al., Science 273 (1996) 663–666). Desert hedgehog (Dhh) is involved in the development of male germ line cells. Further evidence for involvement of hedgehog, e.g. Shh, in bone development and repair is given by mutations leading to human holoprosenphaly (Roessler et al., Human Molecular Genetics 6 (1997) 1847–1853; Belloni et al., Nature Genetics 14 (1996) 353) and by the induction of ectopic bone after expressing Shh in fibroblasts and transplantation of the cells in muscles (Nakamura et al., BBRC 237 (1997) 465–469); Kinto et al., FEBS Letters 404 (1997) 319–323).

Bone morphogenetic proteins (BMPs) are molecules which are responsible for the formation of bone, cartilage, tendon, and other tissues, shown by ectopic bone formation (Wozney et al., Science 272 (1988) 738–741). The unique inductive activities of these proteins, along with their presence in bone, suggest that they are important regulators of bone repair processes and may be involved in the normal maintenance of bone tissue. Many such proteins are known which can be divided into several sub-families (Reddi, A. H., Cytokine & Growth Factor Reviews 8 (1997) 11–20). Such BMPs are, for example, BMP-2 to BMP-14 and the growth and developmental factors GDF-1 to GDF-14.

BMPs are important signaling factors and regulate the multistep sequential cascade in bone and cartilage formation such as chemotaxis, mitosis and differentiation. Especially, BMP-2, BMP-3. BMP-4, BMP-5, BMP-7 initiate chondrogenesis and osteogenesis.

In the case of promoting bone healing, only limited success has been achieved. Currently, large bone defects (orthopedic reconstruction) are treated with either bone or bone powder grafting either autografts or allografts. In addition, in all cases of bone fractures about 5–10% show difficulty in healing, either delayed union (healing only after 6 month) or no healing (non-union still after 9 month) (Einhorn, T. A., Journal of Bone and Joint Surgery, American Volume 77A (1995) 940–956). Allograft bone and bone powder are derived from human donors and can be stored in bone tissue banks, but are limited. Since it is human material, extensive screening for viral (e.g. HIV, HBV, HCV) and bacterial contamination is necessary. Also graft rejections may occur. The material varies in quality depending on donor. The use of autologous bone is often accompanied by morbidity at the graft site (Muschler et al., Clin. Orthop. Rel. Res. (1996) 250–260). In addition there is only a limited amount of such a material available from the autologous donor.

Clinical trials for BMP-2 and BMP-7 alone to promote bone healing have been started. The first results indicate that BMP-2 or BMP-7 seem to be equivalent to bone or bone powder grafts (Boyne, J. Oral Maxillofac. Surg. 53 Suppl 4 (1995) 92; Kirker-Head et al., Clin. Orthop. 218 (1995) 222; Johnson et al., Clin. Orthop. 277 (1992) 229). About 2.5 to 6.8 mg per g matrix are used.

There is a high medical need for improved and enhanced cartilage repair. Current therapies for acute defects (e.g. car or sport accidents), either partial thickness, full thickness or gap defects, are excision, debridement or waiting for very rarely occurring self-healing. There are some therapies under investigation, e.g. mosaic plastic, using autogenous bone/cartilage graft in the shape of a cylinder for large defects. There are a few cell therapy approaches in preclinical and premarketing studies. Autologous chondrocytes isolated during a biopsy are cultivated in vitro as a monolayer (Brittberg et al., N. Engl. J. Med. 331 (1994) 889–895). The dedifferentiated cells are injected under a periosteal flap sutured over the defect in an open knee surgery. Mesenchymal stem cells are in preclinical studies which can differentiate into chondrocytes on an appropriate carrier (U.S. Pat. No. 5,486,359). There exists no easy-to-use therapy yet using a protein or combinations of proteins.

WO 98/30234 describes a composition of BMP and hedgehog proteins. WO 97/21447 describes a combination of osteoinductive bone morphogenetic protein (e.g., BMP-7) and a morphogenetic protein stimulating factor IGF-1 for bone healing. WO 92/09697 describes a combination of BMP and TGF-β for such purposes. Factors healing cartilage either alone or in combination are described in WO 96/14335 (cartilage derived morphogenetic proteins) and WO 97/23612.

Further combinations of factors for bone healing are described in U.S. Pat. No. 5,270,300: osteogenic factor (TGF-beta, TGF-beta and EGF, osteogenin, BMP, +combinations thereof) and angiogenic factor (TGF-beta, angiogenin, angiotropin, FGF-2, PDGF-a and combinations thereof for bone healing; in U.S. Pat. No. 5,629,009: TGF-beta, EGF, or factors derived from demineralized bone matrix (between about 10 and 90% by weight of matrix) combined with FGF or PDGF; in EP-B 0 429 570 by Genetics Institute, Inc.: combination of BMPs (protein or DNA) with different type of carriers. There are also mentioned combinations of BMPs with EGF, FGFs, PDGF, TGF-alpha and TGF-beta.

The invention provides a method for improved induction of the chondro-/osteogenic lineage and promoting cartilage and enhanced bone formation, using MIA, preferably in combination with an osteoinductive protein.

The invention further relates to a method for manufacturing a pharmaceutical composition for induction of the chondro-/osteogenic lineage and the promotion of cartilage and bone formation, wherein a melanoma inhibiting activity factor (MIA) according to the invention is used as an essential component of this pharmaceutical composition. It is further preferred to use a combination of MIA and an osteoinductive protein as essential components. The ratio of osteoinductive protein:MIA is preferably 1:1 to 1:20.

It was surprisingly found that MLA, preferably in combination with an osteoinductive (osteogenic) protein, preferably with a bone morphogenetic protein 2, 3, 4, 5 or 7 or a hedgehog protein, results in cartilage and/or bone formation.

By "osteoinductive protein" is preferably understood an osteogenic protein which induces endochondral bone formation. Chondrocytes produce cartlageneous matrix followed by osteoblasts and osteocytes which produce bone tissue. Early genes of the chondro-/osteogenic lineages, e.g. Cbfa1, are thereby upregulated, and this ultimately leads to the formation of chondrocytes and osteocytes. Such an osteoinduction can be achieved, for instance, through BMPs or hedgehog proteins. BMP-2, BMP-7, or hedgehog protein (Shh, Ihh or Dhh) is preferred. The osteoinductive proteins useful in this invention include also proteins such as TGF-β, BMPs, and TGF-β combined with EGF.

A substance's ability to induce osteogenesis can be tested in a simple manner. For this purpose, for example, pluripotent mesenchymal cells, e.g., C3H10T½ cells, are cultured with and without the potential osteoinductive factor. Controls and treated cells are measured for alkaline phosphatase activity. The activity can be measured photometrically using a suitable colorimetric substrate, e.g., p-nitrophenyl phosphate (Nakamura et al., BBRC 237 (1997) 465–469). Increased activity of alkaline phosphatase is scored as osteoinduction. Alternatively, upregulation of osteocalcin and alkaline phosphatase is measured by RT-PCR using suitable primers for osteocalcin and alkaline phosphatase.

A compound's ability to induce chondrogenesis can be tested in vitro using pluripotent mesenchymal cells, e.g. C3H10T½ or pre-chondrogenic cells, e.g. RCJ3.1C5.18. The cells are cultivated in three-dimensional cultures, e.g. micromass culture with the inductor or a combination of inductors for two to three weeks. Collagen type II as cartilage marker could be proven either by immunocytochemistry using monoclonal antibodies or by Northern blot after RNA isolation. Alcian blue staining proves the existence of proteoglycans. A different method would be to test for aggrecan using specific primers in RT-PCR reaction.

In a further preferred embodiment of the invention, MIA, preferably in combination with an osteogenic protein, can be introduced in the cells via gene therapy methods ex vivo or in vivo. For this method the genes coding for MIA, and optionally, for the osteogenic protein are introduced in one vector, preferably under the control of the same promoter, or in separate vectors. For an efficient expression of MIA and the osteogenic protein, it is necessary to use strong promoters in the vectors. Such promoters are, e.g., PGK or CMV promoters. Preferably, the expression vector consists of such a strong promoter, the full-length mRNA of the chosen gene, e.g., BMP-2, BMP-3, BMP-4, BMP-5, BMP-7, Shh, Ihh, or Dhh, FGF, HGF, PIGF, VEGF, an artificial intron and a poly-A-site. For in vivo application, DNA is either lyophilized to collagen sponges, preferably for osteogenesis, or applied with any other suitable carrier, preferably hyaluronic acid or collagen for application as a gel for chondrogenesis. For ex vivo application, cells of the chondrogenic and osteogenic lineage are transfected with such vectors and subsequently implanted.

The pharmaceutical formulation according to the invention may also include an appropriate matrix, for instance, for delivery and/or support of the composition and/or providing a surface for bone formation. The matrix may provide slow release of MIA, preferably in combination with an osteoinductive protein. Slow release for MIA is possible by combining MIA with a matrix to which MIA is bound in a reversible manner by ionic or hydrophobic interaction. Preferably, the composition includes a matrix which is biocompatible and/or biodegradable. Potential matrices for the compositions contain, for example, hyaluronic acid, alginate, calcium sulfate, tricalcium phosphate, hydroxylapatite, polylactic-coglycolid, polyanhydrides, collagen, or combinations of these, whereby hyaluronic acid, alginate, heparin, coulagen and/or polylactic-coglycolid or derivatives thereof are preferred.

For local bone repair, it is preferred to use MIA or its combination with the osteoinductive protein. It is therefore preferred to use for osteogenesis form-stable matrices in close contact with the progenitor cells. MIA or the combination applied to a three-dimensional matrix like a sponge and put tightly into the defect enable cells, e.g. from periost or bone marrow, to proliferate and differentiate into bone cells which are preferably biodegradable. Preferred materials for such sponges are, for example, collagen, alginate, tricalcium phosphate, hydroxylapatite and combinations thereof.

For the induction of chondrogenesis, it is essential that MIA or its combination with the chondrogenic/osteogenic protein should be directed to the local cartilage defect. Cartilage progenitor cells are derived either from the subchondral bone (in full thickness defects) or from the synovial membrane (in partial thickness defects). The treatment enables the cells to proliferate and to differentiate which results in the synthesis of new cartilage. Mature chondrocytes from the surrounding area could be stimulated, too. To this end, it is expedient that the pharmaceutical composition should be applied directly onto, or into, the cartilage tissue, preferably by local implantation or local injection. Suitably, this is done by means of a syringe. Here, again, the use of a matrix is preferred. However, it is preferred that this matrix, rather than being form-stable, should be flowable like a gel or a paste. Preferably, the flowability is high enough to allow the pharmaceutical formulation to be applied with a syringe.

The dosage regimen will be determined by the attending physician, considering various facts which modify the action of the formulation of the invention. Factors which may modify the action of the formulation include the amount of bone desired to be formed, the site of application, the condition of the damage, the patient's age, sex and diet, the severity of any infection, time of administration, and other clinical factors. The dosage may vary with the type of the matrix used in the reconstitution of bone.

The invention further relates to a process for the production of a pharmaceutical agent which is characterized in that MIA is used as an essential component of this agent. In this process, it is preferred to use 500 µg of MIA per implant or per bolus injection. In a preferred embodiment, the pharmaceutical agent contains in addition an osteoinductive protein. The weight ratio of osteoinductive protein:MIA is preferably 1:1 to 1:20. It is thus preferred to use an excess amount of MIA. In this composition, it is preferred to use about 100 μg of osteoinductive protein and about 500 μg of MIA. The overall amount of MIA and osteoinductive protein is preferably in the range between 200 and 800 μg, referred to gram of matrix protein.

For the cartilage applications, such a pharmaceutical formulation is preferably a gel based on a hyaluronic or collagen matrix. Such a gel is preferably injectable and is applied in an amount of 100 μl to 2 ml per bolus injection. In the case of application in the bone, the use of a collagen sponge is preferred.

The invention further relates to a pharmaceutical composition of this kind. A pharmaceutical composition of this kind can be applied for bone repair, osteogenesis in vivo, especially for the treatment of patients who suffer from bone defects and hence are in need of bone repair as well as for cartilage repair.

A further object of the invention is a pharmaceutical composition containing an expression vector for MIA, and optionally, in addition, for an osteoinductive protein, or a combination of a vector for the expression of MIA with a vector capable of expression of an osteoinductive protein, as well as a method for manufacturing such a pharmaceutical composition.

The following examples and references are provided to aid the understanding of the present invention, the true scope of which is set forth in the appended claims. It is understood that modifications can be made in the procedures set forth without departing from the spirit of the invention.

EXAMPLE 1

In Vitro Cell Assay for Induction of Osteogenic Differentiation

Mesenchymal cells, e.g. C3H10T½ cells are seeded into 96 well plates. After 24 hours, the osteoinductive factor, e.g. hedgehog or BMP, is added alone or in combination with MIA (see Table 1). For control, cells are untreated. After 5 days control and treated cells are analyzed for alkaline phosphatase activity and protein content. Alkaline phosphatase (AP) activity is measured photometrically using p-nitrophenyl phosphate as a calorimetric substrate. Increase in activity is scored as osteoinduction. For hedgehog 0.05 μg/ml was applied. MIA was tested in various concentrations from 0.05 μg/ml to 50 μg/ml.

MIA applied alone did not change the alkaline phosphatase activity. When MIA was applied in combination with hedgehog a synergistic effect was observed resulting in 2.7 fold increase of alkaline phosphatase activity.

TABLE 1

| Factor | μg/ml | mmol PNP/min/mg protein | % of control |
|---|---|---|---|
| Hedgehog | 0.05 | 14.43 | 309 |
| MIA | 50 | 4.26 | 91 |
| MIA | 10 | 3.85 | 83 |
| MIA | 5 | 4.14 | 89 |
| MIA | 1 | 3.98 | 85 |
| MIA | 0.5 | 3.71 | 79 |
| MIA | 0.1 | 3.77 | 81 |
| MIA | 0.05 | 4.86 | 104 |
| Hedgehog + MIA | 0.05 + 50 | 39.23 | 839 |
| Hedgehog + MIA | 0.05 + 10 | 26.60 | 569 |
| Hedgehog + MIA | 0.05 + 5 | 30.57 | 654 |
| Hedgehog + MIA | 0.05 + 1 | 16.11 | 345 |
| Hedgehog + MIA | 0.05 + 0.5 | 20.08 | 429 |

TABLE 1-continued

| Factor | μg/ml | mmol PNP/min/mg protein | % of control |
|---|---|---|---|
| Hedgehog + MIA | 0.05 + 0.1 | 25.09 | 536 |
| Hedgehog + MIA | 0.05 + 0.05 | 21.09 | 451 |
| negative control | | 4.67 | 100 |

EXAMPLE 2

In Vitro Assay for Induction of Cartilage Markers

Chondrocytes of pigs were isolated from femoral condyles. Primary human chondrocytes were isolated from femoral condyles of patients undergoing knee surgery. The cartilage was minced into small pieces and incubated in 10 ml with 2 mg/ml of collagenase (Roche Diagnostics GmbH, DE) and 0.1 mg/ml of hyaluronidase (Sigma) and 0.15 mg/ml DNase (Roche Diagnostics GmbH, DE) for 16 h at 37° C. After centrifugation, the chondrocytes were seeded in petri dishes for proliferation.

The dedifferentiated cells were used for assays. $2 \times 10^4$ cells in 10 μl medium were spotted per well in 96-well plates. After 4 h, 200 μl medium were added. After 7 days, inductors were added to the micromass culture: BMP-2, hedgehog, MIA, and combinations thereof. Two to four weeks later, the cultures were assayed for cartilage markers. Morphologically, chondrocytes are visible by their round appearance. Immunocytochemistry shows collagen type II expression. Cytochemically, Alcian blue proves sulfated proteoglycans. With PCR, aggrecan and SOX9 could be shown.

EXAMPLE 3

In Vitro Assay for Induction of Proliferation

Chondrocytes were isolated from the femoral condyles of pigs. 3,000 cells were seeded in 96 well plates and cultivated for 3 days. After 24 h of serum-free incubation, MIA, BMP-2, Shh and combinations thereof were added. During the last 16 h of the 48 h serum-free induction period, BrdU labeling was present. The detection ELISA was done according to the instructions of the manufacturer (Roche Diagnostics GmbH).

TABLE 2

| factor | ng/ml concentration | % stimulation above serum-free control |
|---|---|---|
| hedgehog | 100 | 88 |
| | 50 | 93 |
| BMP-2 | 500 | 112 |
| | 100 | 69 |
| MIA | 50,000 | 195 |
| | 10,000 | 85 |
| | 2,000 | 99 |
| MIA + BMP-2 | 50,000 + 500 | 125 |
| | 10,000 + 500 | 237 |
| | 50,000 + 100 | 203 |
| | 10,000 + 100 | 133 |
| MIA + hedgehog | 50,000 + 100 | 115 |
| | 10,000 + 100 | 224 |
| | 50,000 + 50 | 261 |
| | 10,000 + 50 | 131 |
| fetal calf serum | | 792 |
| serum-free control | | 100 |

MIA alone and in combination stimulates DNA synthesis of primary chondrocytes.

EXAMPLE 4
In Vitro Organ Assay to Study Chondrogenesis:Mouse Limb Bud Assay

Limb buds are isolated from E12.5 to E15.5 mouse embryos (NMRI) using microdissecton scissors and watchmaker's forceps under sterile conditions. The limb buds were rinsed in PBS containing an antibiotic-antimycotic from Gibco-BRL (#15240-039), then cultured in serum-free BGJb medium from Gibco-BRL (#12591-020) for 48 h to 144 h in organ culture dishes. After 24 h of culture MIA, BMP-2 alone or various combinations of MIA and BMP were added. Media were changed every day. At the end of the culture the limbs were rinsed in PBS, then fixed overnight in 4% paraformaldehyde, either processed for paraffin embedding or for wholemount in situ hybridization as described by Wilkinson, D. G., In situ hybridization: a practical approach, In: Rickwood D, Hames B D (eds.) The practical approach series, Oxford Univ. Press, Oxford, New York, Tokyo (1992). Paraffin sections were stained with von Kossa to visualize and quantitate the amount of calcified areas, stained with Alcian blue to assess chondrogenesis. In addition in situ RNA hybridization was performed to analyze gene expression characteristic for cartilage development, e.g. collagen II, MIA, collagen X.

EXAMPLE 5
Mouse Bioassay for Cartilage, Bone, Tendon and Ligament Induction

Similar to the Sampath and Reddi rat ectopic implant assay, a mouse ectopic implant assay, using inbred C3H mice, 4 months old was performed (Sampath and Reddi, Proc. Natl. Acad. Sci. USA 80 (1983) 6591–695; WO 95/16035). (a) MIA alone, (b) BMP-2 alone and (c) combinations of MIA and BMP-2 were applied in the appropriate buffer, 0.1% trifluoroacetic acid for BMP-2 and 100 mM potassium-phosphate, 150 mM NaCl, pH 6.0 for MIA. As carrier were used collagen type I matrix and hyaluronic acid. Any suitable carrier maybe used, e.g. collagen type I matrix, collagen-heparin mixture, gelatin capsules, hyaluronic acid, alginate or other functionally equivalent device, based on biocompatibility, biodegradability, stability and mechanical properties.

The implants were placed intramuscular into the gluteus muscle of the mouse and left for 14 days. After 14 days the mice were sacrificed by cervical dislocation. The implants were isolated and processed using standard histological techniques (see Theory and Practice of Histological Techniques, ed. Bancroft and Stevens, Churchill Livingstone, 1996). Paraffin sections (4 μm) were cut and stained with von Kossa to visualize and quantitate the amount of cartilage and bone tissue induced in each implant. Positive (e.g. BMP-2) and negative (e.g. mock device) implant control groups were compared to experimental implants.

To assess the quality of cartilage and/or bone induced, gene expression can be studied by RNA in situ hybridization for cartilage and bone markers as described above, using cartilage markers (e.g. collagen II, collagen X) and bone markers (e.g. collagen I, osteocalcin).

EXAMPLE 6
Mouse Bioassay for Cartilage, Bone, Tendon and Ligament Induction for DNA Expression Vectors Similar to the Sampath and Reddi rat ectopic implant assay, a mouse ectopic implant assay, using e.g. outbred NMRI mice or inbred C3H mice, 2 months old was performed (Sampath and Reddi, Proc. Natl. Acad. Sci. USA 80 (1983) 6591–695; WO 95/16035. Expression vectors for (a) osteoinductive factor alone, (b) MIA alone and (c) combinations of osteoinductive factor and MIA were lyophilized in the appropriate buffer, e.g. TE-buffer (Fang et al., Proc. Natl. Acad. Sci. USA 93 (1996) 5753–5758). Any suitable carrier may be used, e.g. collagen type I matrix, collagen-heparin mixture, gelatin capsules, hyaluronic acid, alginate or other functionally equivalent device, based on biocompatibility, biodegradability, stability and mechanical properties.

The implants were set intramuscular into the hindlimb muscle of the mouse for seven and 14 days. After seven and 14 days the mice were sacrificed by cervical dislocation. The implants were isolated and processed using standard histological techniques (see Theory and Practice of Histological Techniques, ed. Bancroft and Stevens, Churchill Livingstone, 1996). Paraffin (4 μm) sections can be stained with Toluidine Blue, Alcian Blue, von Kossa, Movat or Hematoxylin/Eosin to visualize and quantitate the amount of tendon, ligament, cartilage and bone tissue induced in each implant. Positive (e.g. BMP-2, shh expression vector) and negative (e.g. mock device) implant control groups are compared to experimental implants.

To assess the quality of cartilage and/or bone induced, gene expression can be studied by RNA in situ hybridization for cartilage and bone markers as described above.

EXAMPLE 7
Non-Union Fracture Model in Rabbits (Radius Osteotomy)

A non-union defect of 1.5 cm in length was produced at the radius of adult rabbits in order to assess the ability of the combinations of MIA alone and MIA in combination with BMP or hedgehog proteins and appropriate carrier to affect bone repair. The animals were anesthetized by intravenous injection of xylazine/ketamine, and surgery was carried out under sterile conditions. The defect was either left empty, filled with the appropriate carrier, or filled with a carrier containing MIA and BMP, or each of these factors alone. Animals were allowed to move freely and X-rays were carried two and four weeks after surgery in order to assess the rate of bone defect healing. At the end of study, the animals were killed under anesthesia and the bone defect site was removed for histological examination using the von Kossa and Goldner stain so as to quantify and characterize the quality of newly formed repair tissue.

EXAMPLE 8
Full Thickness Articular Cartilage Repair Model

A full thickness articular cartilage defect model in the femoral-patellar joint of adult rabbits is used to assess the ability of MIA alone or in combination with BMP or hedgehog protein and carrier to affect cartilage and bone repair. Adult rabbits are anesthetized and prepared for sterile surgery. An up to 4×4 mm defect through articular cartilage and into underlying subchondral bone is drilled into the patellar groove of the knee joint The defect is either left empty, filled with the appropriate carrier, or filled with a carrier containing MIA alone or in combination with BMP or hedgehog protein. Animals are allowed to move freely for four weeks. After four weeks the animals are humanely euthanized and the articular cartilage/subchondral bone defect site is evaluated histologically for tissue architecture, quantity and quality of the repair.

EXAMPLE 9
Partial Thickness Articular Cartilage Repair Model

A partial thickness articular cartilage defect model in the femoral-patellar joint of adult rabbits is used to assess the ability of MIA alone or in combination with BMP or hedgehog protein and carrier to affect cartilage and bone repair. Adult rabbits are anesthetized and prepared for sterile surgery. An up to 4×4 mm hole is drilled through articular cartilage into the patellar groove of the knee joint, leaving the underlying subchondral bone intact. The defect is either left empty, filled with the appropriate carrier, or filled with a carrier MIA alone or in combination with BMP or hedgehog protein. Animals are allowed to move freely for four weeks. After four weeks the animals are humanely euthanized and the articular cartilage defect site is evaluated histologically for tissue architecture, quantity and quality of the repair.

LIST OF REFERENCES

Belloni et al., Nature Genetics 14 (1996) 353
Bosserhoff et al., Cancer Research 57 (1977) 3149–3153
Bosserhoff et al., Developmental Dynamics 208 (1997) 516–525
Boyne, J. Oral Maxillofac. Surg. 53 Suppl 4 (1995) 92
Brittberg et al., N. Engl. J. Med. 331 (1994) 889–895
DE 196 53 358 A1
Dietz, U., and Sandell, L., J. Biol. Chem. 271 (1996) 3311–3316
Einhorn, T. A., Journal of Bone and Joint Surgery, American Volume 77A (1995) 940–956
Fang et al., Proc. Natl. Acad. Sci. USA 93 (1996) 5753–5758
Hammerschmidt et al., Trends Genet. 13 (1997) 14–21
Johnson et al., Clin. Orthop. 277 (1992) 229
Kinto et al., FEBS Letters 404 (1997) 319–323
Kirker-Head et al., Clin. Orthop. 218 (1995) 222
Lanske et al., Science 273 (1996) 663–666
Muschler et al., Clin. Orthop. Rel. Res. (1996) 250–260
Nakamura et al., BBRC 237 (1997) 465–469
Reddi, A. H., Cytokine & Growth Factor Reviews 8 (1997) 11–20
Roessler et al., Human Molecular Genetics 6 (1997) 1847–1853
Sampath and Reddi, Proc. Natl. Acad. Sci. USA 80 (1983) 6591–695
Theory and Practice of Histological Techniques, ed. Bancroft and Stevens, Churchill Livingstone, 1996
U.S. Pat. No. 5,270,300
U.S. Pat. No. 5,486,359
U.S. Pat. No. 5,629,009
Vortkamp et al., Science 273 (1996) 613–622
Weilbach et al., Cancer Res. 50 (1990) 6981–6986
Wilkinson, D. G., In situ hybridization: a practical approach, In: Rickwood D, Hames B D (eds.) The practical approach series, Oxford Univ. Press, Oxford, New York, Tokyo (1992)
WO 95/03328
WO 95/16035
WO 96/14335
WO 97/21447
WO 97/23612
WO 98/30234
Wozney et al., Science 272 (1988) 738–741
Xie et al., 44th Annual Meeting, Orthopaedic Research Society, Mar. 16–19, 1998, New Orleans, La.

What is claimed is:

1. A method for inducing chondro-/ostrogenic lineage and promoting of cartilage or bone formation in a person comprising administering a therapeutically effective amount of a pharmaceutical composition comprising a melanoma inhibiting activity factor, wherein said melanoma inhibiting activity factor is MIA, and at least one biocompatible or biodegradable matrix selected from the group consisting of hyaluronic acid, alginate, calcium sulfate, tricalcium phosphate, hydroxyapatite, polylactic-coglycolid, polyanhydrides and collagen to a person in need thereof.

2. A pharmaceutical composition comprising a melanoma inhibiting activity factor, wherein said melanoma inhibiting activity factor is MIA, in combination with an osteoinductive protein, wherein said osteoinductive protein is selected from the group consisting of BMP-2, BMP-7 and a hedgehog protein.

3. A pharmaceutical composition as claimed in claim 2, wherein the ratio of osteoinductive protein:MIA is 1:1 to 1:20.

4. A pharmaceutical composition as claimed in claim 2, wherein the composition comprises a biocompatible matrix.

5. A method for inducing chondro-/ostrogenic lineage and promoting of cartilage or bone formation in a person comprising administering a therapeutically effective amount of a pharmaceutical composition comprising a melanoma inhibiting activity factor, wherein said melanoma inhibiting activity factor is MIA, and at least one biocompatible and/or biodegradable matrix selected from the group consisting of hyaluronic acid, alginate, calcium sulfate, tricalcium phosphate, hydroxyapatite, polylactic-coglycolid, polyanhydrides and collagen, wherein the biocompatible matrix is at least one member selected from the group consisting of hyaluronic acid, alginate, collagen, heparin, polylactic-coglycolid and polyactic-coglycolid derivatives.

6. A method of inducting of the chondro-/osteogenic lineage and promoting cartilage and/or bone formation comprising administering an effective amount of a pharmaceutical composition comprising a melanoma inhibiting activity factor, wherein said melanoma inhibiting activity factor is MIA, at least one biocompatible or biodegradable matrix selected from the group consisting of hyaluronic acid, alginate, calcium sulfate, tricalcium phosphate, hydroxylapatite, polylactic-coglycolid, polyanhydrides and collagen, and an osteoinductive protein selected from the group consisting of BMP-2, BMP-7 and a hedgehog protein to a subject.

7. The method as claimed in claim 6, wherein the ratio of osteoinductive protein:MIA is 1:1 to 1:20.

8. The method as claimed in claim 6 wherein said MIA is combined with said biocompatible matrix.

9. The method as claimed in claim 8, wherein said biocompatible matrix comprises at least one member selected from the group consisting of hyaluronic acid, alginate, collagen, heparin, polylactic-coglycolid and polylactic-coglycolid derivatives.

10. A method of treating or repairing at least one of bone or cartilage in a patient comprising administering to a patient in need of bone or cartilage treatment or repair, an effective amount of a melanoma inhibiting activity factor, wherein said melanoma inhibiting activity factor is MIA, to the patient to repair the bone or cartilage.

11. A pharmaceutical composition comprising a melanoma inhibiting activity factor, wherein said melanoma inhibiting activity factor is MIA, and a biocompatible matrix, wherein said biocompatible matrix is a three dimensional sponge prepared from collagen, alginate, tricalcium phosphate, and hydroxyapatite.

12. The pharmaceutical composition of claim 11, wherein the biocompatible matrix comprises at least one matrix material selected from the group consisting of alginate, tricalcium phosphate, hyaluronic acid, and calcium sulfate.

13. A method of treating or repairing at least one of bone or cartilage in a patient comprising administering an effective amount of a composition comprising a melanoma inhibiting activity factor, wherein said melanoma inhibiting activity factor is MIA, and an osteoinductive protein to the patient to repair the bone or cartilage.

* * * * *